(12) United States Patent
Cuozzo

(10) Patent No.: US 6,954,668 B1
(45) Date of Patent: Oct. 11, 2005

(54) APPARATUS AND METHOD FOR INTRA-ORAL STIMULATION OF THE TRIGEMINAL NERVE

(76) Inventor: John W. Cuozzo, 489 Barnsboro Rd., Sewell, NJ (US) 08080

( * ) Notice: Subject to any disclaimer, the term of this patent is extended or adjusted under 35 U.S.C. 154(b) by 431 days.

(21) Appl. No.: 09/975,501

(22) Filed: Oct. 11, 2001

(51) Int. Cl.$^7$ ................................................. A61N 1/36
(52) U.S. Cl. ............................ 607/2; 607/45; 607/149; 607/63; 607/134; 600/26
(58) Field of Search ........................... 607/45, 1, 2, 51, 607/63, 115, 116, 134, 149, 47; 128/898; 600/26

(56) References Cited

U.S. PATENT DOCUMENTS

| | | | | |
|---|---|---|---|---|
| 285,977 | A | * | 10/1883 | Dennis ........................ 607/134 |
| 566,103 | A | * | 8/1896 | Waite ............................. 607/2 |
| 569,380 | A | * | 10/1896 | Hollingsworth ............... 604/20 |
| 3,838,515 | A | * | 10/1974 | Paugh et al. ................... 433/20 |
| 4,175,565 | A | * | 11/1979 | Chiarenza et al. ............. 433/32 |
| 4,649,935 | A | * | 3/1987 | Charmillot et al. .......... 607/134 |
| 5,033,999 | A | | 7/1991 | Mersky |
| 5,447,489 | A | * | 9/1995 | Issalene et al. ................ 600/25 |
| 5,460,593 | A | | 10/1995 | Mersky et al. |
| 5,540,734 | A | | 7/1996 | Zabara |
| 6,034,295 | A | * | 3/2000 | Rehberg et al. ........... 623/23.49 |
| 2003/0069626 | A1 | * | 4/2003 | Lattner et al. ............... 607/134 |

OTHER PUBLICATIONS

John William Cuozzo, *A Correlation Of The Functions And Diameters Of The Sensory Fibers In The Inferior Alveolar Nerve Of The Cat*, Jun. 1996, Thesis Submitted To The Faculty Of Graduate School Of Loyola University For Fulfillment Of The Requirements For The Degree Of Master Of Science.

* cited by examiner

*Primary Examiner*—Kennedy Schaetzle
(74) *Attorney, Agent, or Firm*—Brian F. Russell; Dillon & Yudell LLP

(57) ABSTRACT

An apparatus for intra-oral stimulation of the trigeminal nerve includes an energy source that imparts energy to a tooth to stimulate the trigeminal nerve and an attachment portion to secure the energy source in a mouth in proximity to the tooth. Stimulating the trigeminal nerve in this manner has been experimentally shown to induce and/or enhance relaxation and/or sleep without the adverse side effects associated with traditional drug therapies. In one embodiment, the apparatus can be realized as a "cap" having two legs that engage opposing sides of a tooth and a bridge portion spanning the occlusal surface of the tooth to link the legs.

17 Claims, 3 Drawing Sheets

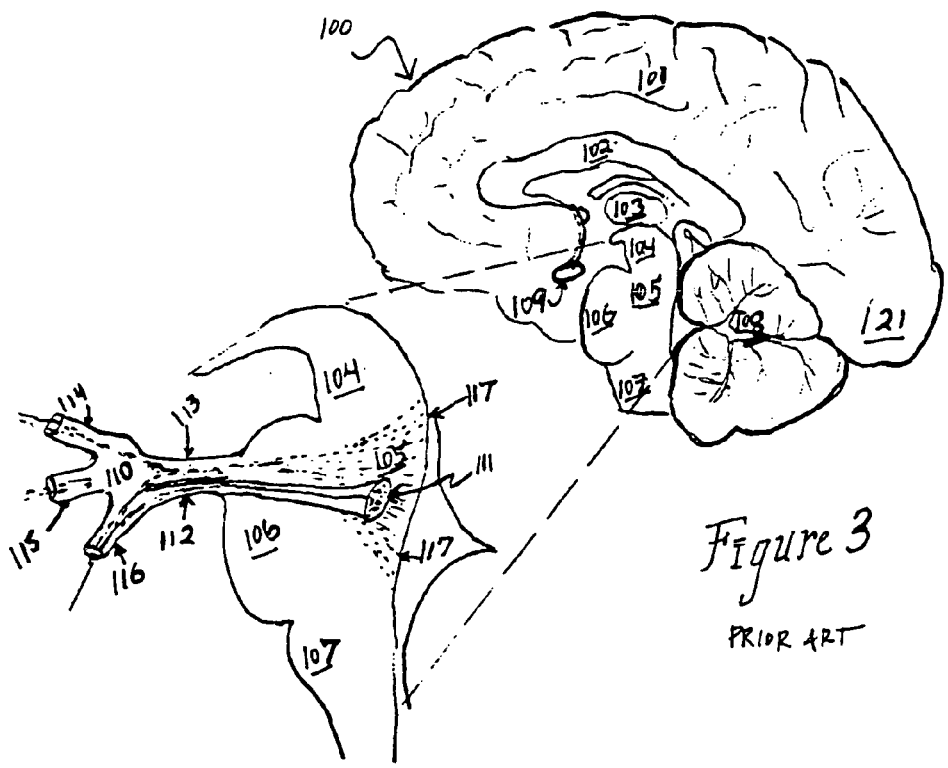
Figure 3
PRIOR ART
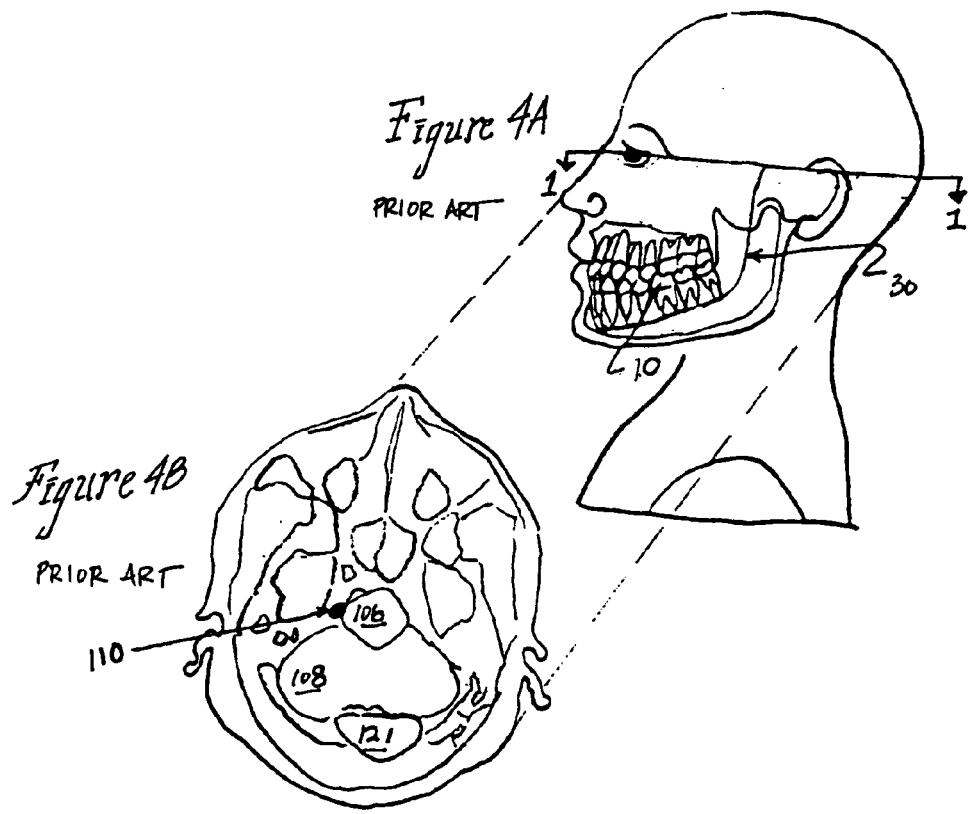
Figure 4A
PRIOR ART
Figure 4B
PRIOR ART

APPARATUS AND METHOD FOR INTRA-ORAL STIMULATION OF THE TRIGEMINAL NERVE

BACKGROUND OF THE INVENTION

1. Technical Field

The present invention relates to an apparatus and method for intra-oral stimulation of the trigeminal nerve.

2. Description of the Related Art

Insomnia has been defined as "the subjective problem of insufficient or nonrestorative sleep despite an adequate opportunity for sleep. It occurs at one time or another in almost all adults."[1] It is a universal problem.

Insomnia has been linked to a reduction in NREM stage 3–4 or delta brainwaves that characterize the deepest pattern of sleep. Delta brainwaves, so named for their association with the four D's of disease, dystrophy, damage and deep sleep, are large and slow with a frequency of less than 4 per second.[2] Electroencephalogram (EEG) measurements indicate that, on average, children and young adults have more NREM stage 3–4 sleep than older adults,[3] and a decrease in Stage 3–4 NREM sleep is a typical symptom of aging past age 55.[4]

Insomnia can be addressed in a variety of ways. First, a number of appliances are available to reduce or eliminate physiological impediments to the body's natural sleep cycle.

Appliances for sleep therapy principally address lung, breathing (e.g., genioglossus contraction failure during inspiration) and snoring problems, which commonly accompany sleep disorders such as sleep apnea. Second, sleep therapies are available that are intended to induce sleep. Such sleep therapies include well-known drugs, such as benzodiazapines (e.g., lorazepam and flurazepam). Unfortunately, these drugs create physical dependence, often cause adverse reactions, and require higher dosages as tolerance increases with use. Discontinuation of benzodiazapine use is very difficult, and withdrawal symptoms have been reported months after use of even low dosages. Perhaps as a consequence of the negative side effects of drug therapies, melatonin, a hormone naturally occurring in the brain, is taken by millions of Americans to induce sleep with varying rates of success.

In view of the widespread incidence of insomnia and the absence of a sleep therapy that is generally successful in inducing sleep without side effects, the present invention therefore recognizes that it would be useful and desirable to provide a sleep therapy that successfully induces sleep without the negative side effects that accompany traditional drug therapies.

Another common problem experienced by millions of Americans is that of chronic stress, which can defined as frequent activation of the body's natural adrenal response in response to circumstances that do not warrant "fight or flight." Chronic stress is characterized by accelerated pulse and respiration rates and is a significant risk factor for heart disease, the leading cause of death in the U.S.

Conventional methods of addressing stress include, among others, drug therapies, relaxation and meditation techniques, and lifestyle changes. As with the drug therapies for insomnia, the drug therapies for stress (and the related malady of anxiety) can have significant adverse side effects. Consequently, sufferers of stress often turn to alternative methods of addressing stress, such as lifestyle modification and relaxation and meditation techniques. However, these alternatives do not alleviate the chronic stress for all individuals or in all circumstances. Therefore, a need remains for a stress therapy that successfully alleviates stress and induces relaxation without the negative side effects that accompany traditional drug therapies.

It should also be noted that it is known to control or treat medical, psychological or neurological disorders (including sleep disorders) by application of electrical signals directly to the afferents of a patient's trigeminal and/or glossopharyngeal nerves. For example, U.S. Pat. No. No. 5,540,734 to Zabara discloses an implantable or external neurostimulator (i.e., generator) that can be utilized to directly stimulate the afferents of the trigeminal and/or glossopharyngeal nerves of a patient to treat sleep disorders, eating disorders, neuropsychiatric disorders, and a host of other ailments.

In order to provide better understanding of Zabara's teaching, reference is now made to FIG. 3, which illustrates a median sagittal section of a human brain 100. Brain 100 comprises a number of major structures, including cerebral hemisphere 101, occipital gyrus 121, optic chiasma 109, corpus callosum 102, cerebellum 108, third ventrical 103, cerebral peduncle 104, medulla oblongata 107, mesencephalon (midbrain) 105, and pons 106. As shown in the expanded view, the sensory nuclei 117 and motor nucleus 111 of the trigeminal nerve are embedded in mesencephalon 105. The motor root 112 and sensory root 113 of the trigeminal emerge through pons 106 and merge to form trigeminal (Gasserian) ganglion 110, which then divides into the ophthalmic, maxillary, and mandibular divisions 114–116 of the trigeminal nerve. Zabara teaches the stimulation of the trigeminal nerve through electrodes attached directly to one of ophthalmic, maxillary, and mandibular divisions 114–116 or to trigeminal (Gasserian) ganglion 110. As will be appreciated upon inspection of FIG. 3 and also FIG. 4B, which depicts a cross-section of the human brain taken along line 1—1 of FIG. 4A, Zabara's technique requires highly invasive surgery to the center of the brain through some of its most delicate structures in order to attach electrodes to the trigeminal nerve.

The invasive nature of the surgery required to implant electrodes attached to the afferents of the trigeminal and/or glossopharyngeal nerves and the high risk of disabling complications and side effects suggest that the treatment disclosed by Zabara should be reserved for extreme cases, and then only under the close supervision of a medical professional. Consequently, there remains a need for a therapy for treating or controlling sleep disorders and/or stress that is non-invasive and appropriate for the millions of individuals that suffer from sleep disorders and stress.

SUMMARY OF THE INVENTION

The present invention addresses the foregoing and additional shortcomings in the prior art by introducing an apparatus and method that provide an effective, non-invasive relaxation and sleep therapy without the adverse side effects concomitant with traditional drug therapies.

According to one preferred embodiment of the present invention, an apparatus for intra-oral stimulation of the trigeminal nerve includes an energy source that imparts energy to a tooth to stimulate the trigeminal nerve and an attachment portion to secure the energy source in a mouth in proximity to the tooth. Stimulating the trigeminal nerve in this manner has been experimentally shown to induce and/or enhance relaxation and/or sleep without the adverse side effects associated with traditional drug therapies. In one embodiment, the apparatus can be realized as a "cap" having two legs that engage opposing sides of a tooth and a bridge portion spanning the occlusal surface of the tooth to link the legs.

Additional objects, features, and advantages of the present invention will become apparent from the following detailed written description.

BRIEF DESCRIPTION OF THE DRAWINGS

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

FIG. 3 depicts a median sagittal section of the human brain, including a close-up schematic representation of the exit of the trigeminal nerve from the pons;

FIG. 4A illustrates a lateral partial sectional view of the human head with maxillary and mandibular teeth in normal occlusion; and FIG. 4B depicts a cross-section of the human cranium taken along line 1—1 of FIG. 4A.

DETAILED DESCRIPTION OF A PREFERRED EMBODIMENT

I. Theory

A. Innervation of the Periodontium

Figure 1:
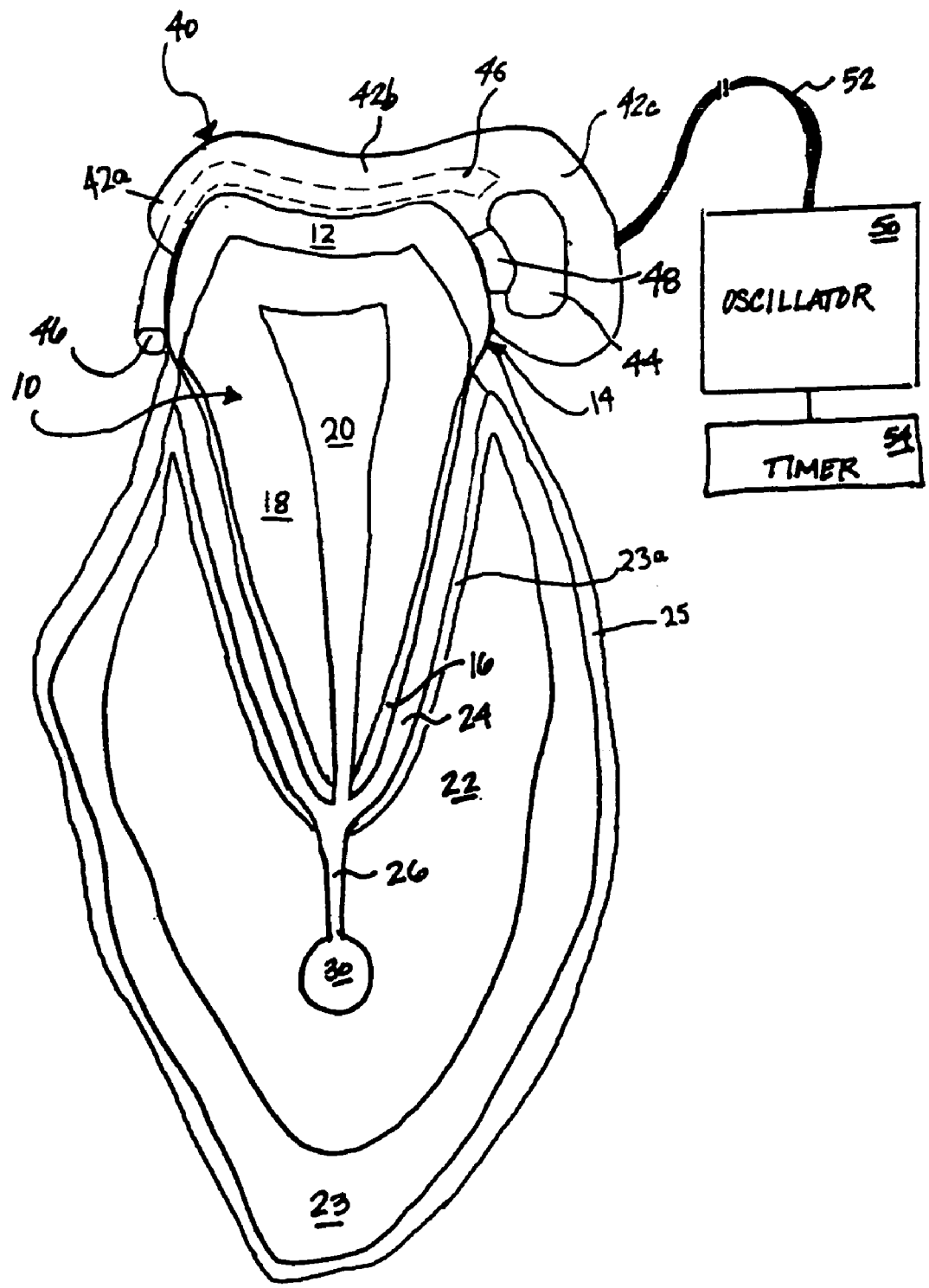
FIG. 1 depicts a sectional view of a tooth to which an intra-oral appliance in accordance with the present invention is attached.

In 1957, Bernick investigated human and monkey periodontium and confirmed that there are two main groups of neural bundles coming from the periodontium: one entering at the apex of the tooth and the other entering through the cribriform plate.[5] He also observed spindle-like nervous structures in the apical third of the ligament, nerve endings terminating in the cementum, and fine unmyelinated fibrils forming a network in the periodontal ligament. In 1923, Gerard described the trigeminal or fifth cranial nerve as follows: "The trigeminal nerve is composed of a large sensory division whose unipolar cells are located in the Gasserian ganglion, and a small motor division distributed entirely through the mandibular branch of the nerve. The skin of the face and the mucous membrane of the mouth, tongue, and nose are supplied by pain, tactile and thermal branches which pass into all three branches of the trigeminal nerve; these are the opthalmic, maxillary, and mandibular nerves. Sensory fibers also accompany the motor root into the brain stem, their unipolar cells of origin forming the mesencephalic nucleus, which is an unusual location for the sensory cells. These fibers are believed to supply the muscles innervated by the motor division of the trigeminal nerve. The main sensory root carries the usual cutaneous sensation."[6] Corbin and Harrison in 1940 described the trigeminal as the great cutaneous sensory nerve of the face, the sensory nerve to the mucous membranes, and other internal structures of the head. They noted that the nerve has two roots: a main sensory and a motor root, which includes, in addition to the motor fibers, proprioceptive sensory fibers from the mesencephalic nucleus.[7]

B. Mesencephalic Nucleus

Thelander in 1924 described the mesencephalic nucleus of the trigeminal nerve as a narrow band of cells situated laterally between the central gray and the mesencephalic reticular formation of the mesencephalon (reference numeral 105 of FIG. 3). The mesencephalic nucleus extends from the posterior commisure to below the level of the trigeminal motor nucleus. The cells of the mesencephalic nucleus are predominately unipolar and have been compared to spinal ganglion cells. The similarities between the cells of the mesencephalic nucleus and the spinal ganglia as first order neurons have also been pointed out.[8] The studies of Corbin and Harrison further added to the clarification of the function of the mesencephalic nucleus. They demonstrated the peripheral distribution of the fibers from this area and showed that the nucleus is activated by jaw opening movements and pressure stimulation of teeth and soft tissue in the mouth.[9] Jerge discovered three types of neurons in the mesencephalic nucleus. He classified two types of dental pressoreceptors and one type of muscle proprioceptor. The first type of dental pressoreceptor represented activity from a single tooth that had been stimulated. The second type of pressoreceptor represented activity from a group of stimulated teeth and from adjacent soft tissues.[10]

C. Nerve Fibers in the Trigeminal Nerve of the Cat

Gerard in 1923 sectioned the trigeminal nerve of the cat, which has been found to be of similar construction and function to corresponding human nervous structures. Gerard stated: "In cross-section the nerve was seen to consist of fibers varying from the unmyelinated ones of 1.5 microns to the largest myelinated fibers of 16 microns in diameter. These latter belonged to the motor root and were always found on the dorsal surface of the nerve. There were very few of them, only 46 and 42 in two nerves counted, the majority of the motor nerves being between 10.8 and 11.7 microns in diameter."[11] He asserted that the majority of the sensory fibers in the nerve trunk ranged from 5.3 to 8 microns. Brashear found the largest fibers in the inferior alveolar nerve of the cat to be 16 microns.[12] He also found the pulpal nerve fibers to only be as large as 9 microns. Windle in 1927 said, "since practically no large myelinated fibers and few unmyelinated ones pass into the pulp cavity, these must belong to the nerves innervating the periodontal membrane and gums."[13]

D. Pressure Response

Duval in 1833 showed that the dentin is acutely sensitive to pain, and this remains the presently accepted view.[14] Peaselee in 1857 mentioned that pressure can be detected and localized by individual teeth. He emphasized that this power of localization was due to the innervation of the periodontal ligament and was still present after removal of the pulp.[15] Stewart in 1927 demonstrated that the tactile thresholds of teeth were practically unchanged after removal of their pulps. Pfaffman in 1939 was the first person to use electrophysiologic methods to register the action potentials in the dental nerves of the cat. He recorded afferent impulses from the teeth, which were induced by graduated force applications and noxious stimuli. He again concluded (in agreement with almost everyone) that the tactile receptors are located in the periodontal ligament and enter through the cribriform plate. He believed this because the tactile responses that he recorded diminished very little after he destroyed the apical nerve coming out of the tooth by cautery.[16]

Contradictory evidence was presented by Loewenstein and Rathkamp in 1955 in their studies of human teeth with pulps removed. They found higher threshold values (diminished tactile responses) in pulpless teeth. In an attempt to determine the location of the dental pressoreceptors, the normal tooth to be examined was covered with a metallic crown. Pressure tests on these teeth revealed a slightly diminished response compared to normal uncrowned teeth. Vital and pulpless teeth that were covered by metal crowns showed no differences at all. These results were based upon conscious perception of stimuli by individuals rather than electrical impulses recorded from nerve trunks, which provide more accurate data. Based upon these studies, it can be concluded that pressoreceptors are removed in vigorous pulp removal extending too far through the apex of a tooth, or that the results of Loewenstein and Rathkamp were inaccurate due to subjective data collection methods, or that some sensitivity to pressoreception resides in the pulp of a tooth. Of these three possibilities, the first two appear most likely.

E. Sensory Fibers in the Inferior Alveolar Nerve of the Cat

During a physiologic investigation of the inferior alveolar nerve of the cat, diphasic action potentials resulting from tapping the incisal edge of the mandibular canine tooth with forces greater than 4 grams were recorded by means of silver electrodes attached to the inferior alveolar nerve where it exits from the mandibular foramen. If the force was maintained, higher initial spikes were observed, followed by smaller spikes having an asynchronous pattern. When the sustained force was removed, a brief high voltage discharge was occasionally observed. It was presumed that the origin of these potentials was the periodontal ligament. These potentials were superimposed on the background potentials of lesser magnitude. Increases in applied force beyond 40 grams caused only moderate increases in amplitude. It is believed that as heavier forces were applied to the tooth more nerve fibers were recruited to communicate the sensed pressure. According to Gasser in 1934,[17] Ruch and Patton in 1965[18], Boyd in 1954[19], and Hunt in 1954[20], the lightest force first recruits the fastest nerve fibers, which are the ones with the largest diameters.

When cross-sectioned, it was found that the nerve fibers of the inferior alveolar nerve of the cat varied in diameter from 0 to 16 microns. The mean percent of the 14–16 micron fibers in the nerve sections was 2.26% of the total mean. Those between 6 and 14 microns comprised 48.56% of the total, with 49.18% of the fibers were below 6 microns. These smaller fibers are believed to be associated with the periodontal ligament pain responses. The 6 to 14 micron group comprises thermal fibers from the oral cavity, pulpal fibers, and tactile fibers from the gingiva. Relevant to the present discussion is that the tactile, mechanoreceptor or proprioceptive receptor has as its route of conduction in the largest (i.e., 14–16 micron) fibers, which are the fewest and respond to the lightest touch.

F. Tooth as Piezoelectric Conductor

The mandibular first molar tooth 10 is depicted within the lateral partial sectional view of the human head provided in FIG. 4A. As illustrated in the cross-sectional buccolingual view of the mandibular first molar provided in FIG. 1, every human tooth 10 is a composite structure formed of different materials. The exposed surface of tooth 10 is covered with enamel 12 to gumline 14 or even slightly below gumline 14. Below gumline 14, the surface of the root(s) of tooth 10 is covered with cementum 16. (Only the distal root of the mandibular first molar is shown in FIG. 1.) The interior of the tooth 10 underneath enamel 12 and cementum 16 is formed of dentin 18. Finally, in the interior cavity of tooth 10 is pulp 20, which includes the pulpal nerves.

The root of tooth 10 is anchored in mandibular cancellous bone 22 and cribriform plate 23a within an outer cortical plate 23 by periodontal ligament 24. Periodontal ligament 24 is attached to a nerve bundle 26, which receives nerve fibers from both periodontal ligament 24 and pulp 20 and conducts nerve impulses to the mandibular branch of the trigeminal nerve 30 (which is also depicted at reference numeral 30 of FIG. 4A and at reference numeral 116 of FIG. 3). Layers of connective tissue/membrane 25 cover the lamellated cortical plate 23.

When enamel 12 first develops, enamel 12 is formed of tightly packed columns or "matrix" of a relatively soft fibrous material like that of tendons and ligaments. During subsequent human development, minerals (almost exclusively calcium and phosphorous) bond within the matrix to form hydroxyapaptite crystals, also called "apatites." These mineral crystals harden within the matrix to form a combination of hard and soft materials called the enamel "prism" or "rod, " which extends from the dentin interface to at or near the outermost surface of enamel 12. At the completion of development, enamel 12 is formed of approximately 95–97% minerals by weight, which makes enamel 12 very hard.

Athenstaedt in 1971 discovered that pressure stimulation of a tooth produces a piezoelectric effect. He found that even if you slice a tooth into thin cross-sections horizontally, positive and negative charges are elicited with pressure stimulation.[21] He wrote that, "Under the effect of compression, a complete tooth has a positive charge at the occlusal surface and a negative electric charge at the root apex (piezoelectric effect)."[22]

II. Application of Theory

By synthesizing the foregoing information, the present invention recognizes that the pressoreceptors within periodontal ligament 24 and therefore trigeminal nerve 30 (see also FIG. 4A) can be stimulated by application of an external energy source to enamel 12. The enamel prisms first resonate when energy is applied, for example, by a mechanical, sonic or electromagnetic energy source. Because of the hardness of the hydroxyapaptite crystals of enamel 12 and the size of the crown of tooth 10, tooth 10 has a high resonance Q.[23] As a result, tooth 10 is frequency-selective and is slow to respond to a driving signal, but sustains its activity for some time after an interval of forced oscillation.

The prisms of enamel 12 conduct the energy to dentin 18 and cementum 16. Dentin 18 and cementum 16 act as plates of a piezoelectric speaker, conducting the resonance via cementum 16 into periodontal ligament 24. The pressoreceptor nerve endings within nerve bundle 26 that are stimulated by the induced resonance are the largest ones (about 2–3% of the total bundle), which conduct the lightest forces. These nerve endings conduct the stimulation to the mandibular branch of the trigeminal nerve 30, thus providing a direct route to the midbrain. By stimulating the midbrain in this fashion, delta brainwaves can be induced, leading to relaxation and/or sleep.

Figure 2:
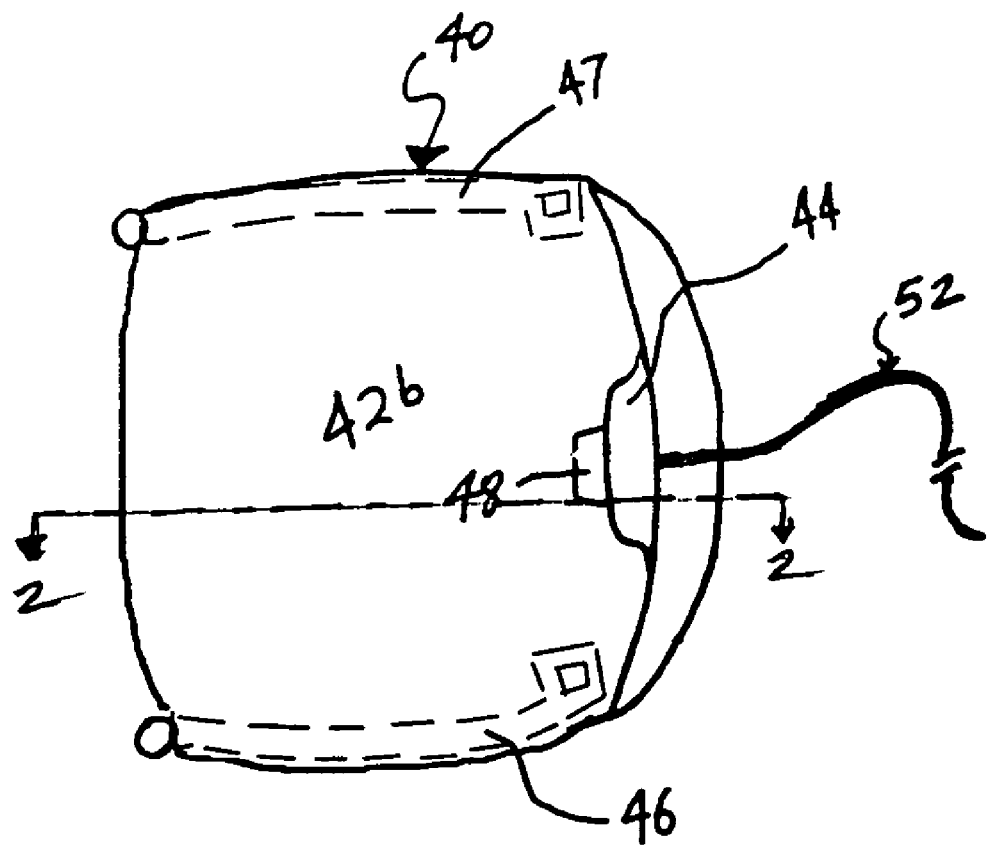
FIG. 2 illustrates an occlusal plan view of an intra-oral appliance in accordance with a preferred embodiment of the present invention, wherein line 2—2 identifies the location of the section view of FIG. 1.

In accordance with a preferred embodiment of the present invention and as illustrated in FIGS. 1 and 2, energy is applied to tooth 10 to stimulate the trigeminal nerve by a removable and reinstallable intra-oral appliance 40. Appliance 40 includes an energy source 44 and an attachment portion 42 that removably secures energy source 44 in close contact with enamel 12 (or if tooth 10 has an artificial crown, to the artificial crown).

In the depicted embodiment, attachment portion 40 includes a first leg 42a, a slightly longer second leg 42c, and a bridge portion 42b spanning the occlusal surface of tooth 10 to link first and second legs 42a and 42c. As illustrated in FIG. 1 in phantom, bridge portion 42b includes an embedded standard 0.040-inch diameter stainless steel orthodontic wire 46. As depicted in the occlusal plan view provided in FIG. 2, bridge portion 42b also includes a similar second embedded wire 47. When appliance 40 is installed, wires 46 and 47 respectively engage the distal and mesial inferior lingual surfaces of the crown of tooth 10 below the widest portion of the crown. Attachment portion 40 is thus removably retained on tooth 10 by the spring force of wires 46 and 47 and interference fit of the contact portion 48 of energy source 44 with the buccal side of tooth 10.

Attachment portion 40 is preferably fabricated by a dental health professional from lightly cured or self-cured acrylic or other durable non-toxic material to ensure a proper fit that permits easy installation, removal, and reinstallation of appliance 40. Because the muscles of mastication (except external ptyergoid M) send proprioceptive nerve fibers into the mesencephalic nucleus, the stretching of these muscles much beyond their resting length will send interfering impulses into the same nerve nucleus that appliance 40 stimulates. The stimulation of these muscles with appliance 40 installed should therefore be minimized or avoided by sizing appliance 40 so that the bite is not opened a great deal with appliance 40 installed.

As noted above, energy source 44 can be implemented as a mechanical, sonic or electromagnetic energy source. In a typical implementation, energy source 44 is a transducer coupled by electrical conductors 52 to an external power source, such as oscillator 50. For example, in one exemplary embodiment, energy source 44 comprises an electromagnetic coil, such as commonly found in acoustic earphone speakers, and oscillator 50 comprises a portable electronic device (e.g., audio cassette player, CD player, MP3 player, etc.) that outputs low voltage analog audio frequency electrical signals via electrical conductors 52. These electrical signals are converted by the electromagnetic coil into a time-varying magnetic field that, due to the piezoelectric properties of tooth 10 discussed above, stimulates trigeminal nerve 30. In an alternative embodiment, energy source 44 can be implemented as a mechanical vibrator that vibrates at a frequency determined by an input signal received from oscillator 56.

In each of these possible embodiments, it is preferable, though not required, for the frequency range of electrical signals output by oscillator 50 to be calibrated to the resonant frequency of the specific tooth 10 on which appliance 40 is to be installed in order to achieve the maximal effect in the pressoreceptors, trigeminal nerve fibers and brain stem. It has also been found helpful to vary the amplitude and frequency of the stimulation provided by energy source 44 between uses.

In use, one or more teeth can be employed to stimulate the trigeminal nerve at a time. It is preferable, however, that only one side of the dental arch is employed at a time because impulses entering the main nerve trunk from opposite sides of the inferior or superior alveolar branches of the trigeminal nerve will tend to block each other. In addition, the effectiveness of appliance 40 is improved if use is limited in duration (e.g., approximately 30 minutes) because the wake cycle in the reticular formation of the brain is triggered if stimulation of the trigeminal nerve continues after delta waves characteristic of deep relaxation or sleep have been induced. Thus, the best response results from a metered dose, which will depend on the size of the tooth, number of teeth employed, and the individual's sleep habits and therapeutic history (e.g., previous drug therapies). Accordingly, it is useful if oscillator 50 has an associated timing mechanism, such as timer 54, to conveniently meter the duration of use. In experimentation, it has also been found helpful to alternate sides of the dental arch (e.g., alternating between the right and left first mandibular molars) approximately every seven days because the affected nerves appear to adapt to the stimulus over a period of about a week. Alternating sides, which would preferably entail the alternating use of different appliances 40 for the right and left sides, enhances the effectiveness of the therapy and maintains a high level of response on both sides of the dental arch.

As has been described, the present invention provides an intra-oral appliance for stimulating an alveolar branch of the trigeminal nerve through the pressoreceptors of one or more teeth. By doing so, relaxation and/or sleep can be induced and/or enhanced. Other beneficial applications are also contemplated. For example, stimulating the pressoreceptors of the teeth has been found to inhibit jaw muscle activity by relaxing the elevator jaw muscles (temporalis, internal ptyergoid and masseter).[24] Consequently, the appliance of the present invention has application to patients with TMJ (temporomandibular joint) problems and/or bruxism (i.e., teeth grinding). It is expected that further experimental use will confirm additional applications of the appliance of the present invention, which applications include those previously addressed by direct electrical stimulation of the trigeminal nerve as taught by Zabara in U.S. Pat. No. 5,540,734, the pertinent parts of which are incorporated herein by reference. These additional applications are within the scope of the present invention.

Although the present invention and that of Zabara have common uses, several significant differences between Zabara and the present invention should be noted. First, Zabara's technique can lead to the contraction of the muscles of mastication, unlike the present invention, which relaxes them. One site for electrode placement recommended by Zabara is the mandibular (third) division 116 of the trigeminal nerve. In contrast to the ophthalmic and maxillary divisions 114–115 of the trigeminal (see FIG. 3), which carry only sensory impulses, mandibular division 116 carries both motor and sensory impulses, including motor impulses for the main muscles of mastication (e.g., masseters, internal and external pterygoids and temporal muscles). The placement of an electrode on the motor nerves that innervate the mastication muscles as taught by Zabara will send electrical impulses down the nerve to the mastication muscles as well as up the nerve to mesencephalon 105, resulting in (possibly uncomfortable) contraction of the muscles of mastication. As noted above, the present invention, by contrast, relaxes the muscles of mastication.[25]

Second, and more importantly, Zabara's technique is surgically invasive to the midbrain and requires direct nerve contact, while the present invention is completely non-invasive and does not utilize any direct nerve contact. As noted above, while Zabara teaches the use of either an internal or external neurostimulator (electrical signal generator), Zabara's electrodes are always attached directly to the afferents of the trigeminal and/or glossopharyngeal nerves, requiring surgical implantation of the electrodes within the patient's cranial cavity. The present invention, by contrast, can be practiced completely non-invasively without any direct nerve contact. Consequently, oral and cerebral tissues remain intact and undisturbed, reducing the risk of side effects and complications (e.g., infection).

While the invention has been particularly shown and described with reference to a preferred embodiment, it will be understood by those skilled in the art that various changes in form and detail may be made therein without departing from the spirit and scope of the invention. Without restricting the generality of the foregoing, alternative embodiments of the present invention may employ different designs of the intra-oral attachment portion, including "caps" covering multiple teeth. In addition, energy source 44 can be embedded in any oral appliance, including any (1) bite splint, nightguard, mouthguard, or bruxism appliance, (2) TMJ appliance (3) orthodontic brace, bonded bracket or bonded attachment, (4) orthodontic or other type of retainer, or (5) bionator. Furthermore, although the embodiment illustrated in FIG. 1 depicts an oscillator 50 and timer 54 separate from the attachment portion 40 and connected thereto by wires 52, one or both of the oscillator and timer may be integral to the attachment portion and external components, if any, may communicate with the intra-oral components via wireless (e.g., RF) signals. Moreover, although the present invention has been described with reference to an embodiment in which the first mandibular molar is employed, the scope of the present invention encompasses the stimulation of the trigeminal nerve through (1) any tooth or any combination of teeth to which neurostimulation can be applied, (2) any artificial or natural implant in the alveolar or basal bone (maxilla or mandible) that may indirectly affect the inferior or superior alveolar nerves, (3) full or partial dentures or dental bridges that may indirectly affect the inferior or superior alveolar nerves, (4) intra-oral soft tissues, and (5) tongue.

In alternative embodiments of the present invention in which a dental implant, dentures or a bridge is employed to stimulate the trigeminal nerve, an attachment portion similar to that illustrated in FIGS. 1 and 2, but modified to attach to the selected oral structure, can be employed. However, if stimulation is applied directly to intra-oral soft tissues, the intra-oral transducer need not be packaged in an attachment portion, but can instead be maintained in place manually or by the patient's bite.

[1]Ganong, W. F, *Review of Medical Physiology*, 16th Ed. 1993, Appleton & Lange Co, East Norwalk, Conn., p. 181.

[2]Ganong, W. F., p. 180.

[3]Ganong, W. F., p. 175.

[4]Guilleminault, C. and Brown, P. R., Sleep, in Swash, M. and Kennard, C., *Scientific Basis of Clinical Neurology*, Churchill Livingstone, London, 1985, p 298.

[5]Bernick, S. Innervation of the teeth and periodontium after enzymatic removal of collagenous elements. Oral Surg. Oral Med, Oral Path., 1957, 10: pp. 323–332.

[6]Gerard, M. W., Afferent impulses in the trigeminal nerve. AMA Arch. Neur. Psychiat. 1923, 9: pp. 306–338.

[7]Corbin, W. K. and Harrison, F., The function of the mesencephalic root of the fifth cranial nerve. J. Neurophysiol., 1940, 3: pp. 423–435.

[8]Thelander, J. E, The course and distribution of the Radix Mesencephalica Trigemini in the cat. J. Comp. Neurol, 1924, 37: pp 207–220.

[9]Corbin and Harrison, supra.

[10]Jerge, C. R., Organization and function of the trigeminal mesencephalic nucleus. J. Neurophysiol., 1963, 26: pp. 379–392.

[11]Gerard, supra.

[12] Brashear, A. D. The innervation of the teeth. An analysis of nerve fiber components of the pulp and periodontal tissues and their probable significance. J. Comp. Neurol., 1936, 64: pp. 169–185.

[13]Windle, W. F., The distribution and probable significance of unmyelinated nerve fibers in the trigeminal nerve of the cat. J. comp. Neurol., 1926, 41: pp. 453–477.

[14]Duval, J. R, Observations practiques sur la sensibilté des substances dures des dentes. Mem. de l'Acad. Roy. de Med., 1883, 2: pp. 197–205.

[15]Peaselee, E. R, *Human Histology*. Philadelphia, 1857.

[16] Pfaffman, C., Afferent impulses from the teeth due to pressure and noxious stimulation. J. Physiol., 1939, 15: pp. 3–34.

[17]Gasser, H. S., Conduction in nerves in relation to fiber types. Res. Publ. Ass. Nerv. Ment., 1934, 15: pp. 35–59.

[18]Ruch, T. C., Patton, H. D., *Physiology and Biophysics*, ed. 19, Philadelphia, 1965, W. B. Saunders, pp. 83.

[19]Boyd, L. A. The histologic structure of the receptors in the knee joint of the cat correlated with their physiologic response. J. Physiol., 1954, 124:476488.

[20]Hunt, C. C. Relation of function to diameter in afferent fibers of muscle nerves. J. Gen. Physiol., 1954, 38: pp. 117–131.

[21]Athenstaedt, H. Pyroelectric and Piezoelectric behavior of human dental hard tissues, Arch. Oral. Biol., 1971, 16: pp. 495–501.

[22]Ibid.

[23]Benson, K. Blair, *Audio Engineering Handbook*, 1988, McGraw-Hill, Inc. p. 1.25.

[24]Sessle, B. J. and Schmitt, A., Effects of controlled tooth stimulations on jaw muscle activity in man. Arch. Oral Biol. 1972, 17: pp. 1597–1607.

[25]Ibid.

What is claimed is:

1. An apparatus for intra-oral stimulation of the trigeminal nerve, said apparatus comprising:
    a transducer that imparts energy to a tooth to stimulate the trigeminal nerve;
    a time-varying signal source coupled to said transducer to provide a time-varying electrical signal to said transducer;
    an attachment portion to secure said transducer in a mouth in proximity to the tooth; and
    a timer that automatically discontinues provision of said electrical signal to said transducer following a selected interval of provision of said electrical signal.

2. The apparatus of claim 1, wherein said transducer comprises a wire coil.

3. The apparatus of claim 1, said attachment portion comprising:
    a first leg to which said energy source is attached;
    a second leg; and
    a bridge portion spanning a width of the tooth to link said first leg and said second leg.

4. The apparatus of claim 3, wherein said bridge portion includes at least one wire to secure the apparatus about a crown of the tooth.

5. The apparatus of claim 3, wherein said bridge portion includes means for covering an occlusal surface of a crown of the tooth.

6. The apparatus of claim 1, wherein said attachment portion is at least partially formed of acrylic.

7. The apparatus of claim 1, wherein said attachment portion removably secures said electrical transducer in contact with enamel of the tooth.

8. A method of stimulating the trigeminal nerve, said method comprising:
within a mouth, removably securing an energy source it proximity to a tooth;
imparting energy to enamel of the tooth to stimulate the trigeminal nerve utilizing energy source; and
thereafter, automatically discontinuing impartation of energy to said enamel after a selected interval.

9. The method of claim 8, wherein said energy source comprises a transducer, said method further comprising coupling the transducer to an time-varying signal source that provides an electrical signal to the transducer.

10. The method of claim 8, wherein said step of imparting energy to enamel of a toot comprises imparting electromagnetic energy to the enamel of the tooth.

11. An apparatus for intra-oral stimulation of the trigeminal nerve, said apparatus comprising:
a transducer that imparts energy to an oral tissue to stimulate the trigeminal nerve;
an oral appliance supporting said transducer;
a time-varying signal source coupled to said transducer to provide a time-varying electrical signal to said transducer; and
a metering device that automatically discontinues provision of said electrical signal to said transducer following provision of a selected quantum of said electrical signal.

12. The apparatus of claim 11, wherein said transducer comprises a wire coil.

13. The apparatus of claim 11, wherein said oral appliance comprises a dental appliance.

14. The apparatus of claim 11, wherein said metering device comprises a timing device.

15. The apparatus of claim 11, wherein said time-varying signal source comprises an oscillator.

16. The apparatus of claim 11, the oral appliance including an attachment portion for removably securing said transducer in proximity to a tooth.

17. The apparatus of claim 16, said attachment portion comprising:
a first leg to which said transducer is attached;
a second leg, and
a bridge portion spanning a width of the tooth to link said first leg and said second leg.

* * * * *

UNITED STATES PATENT AND TRADEMARK OFFICE
CERTIFICATE OF CORRECTION

PATENT NO. : 6,954,668 B1
DATED : October 11, 2005
INVENTOR(S) : Cuozzo, J.

It is certified that error appears in the above-identified patent and that said Letters Patent is hereby corrected as shown below:

<u>Title page,</u>
Item [56], References Cited, OTHER PUBLICATIONS,
"John William Cuozzo" reference, replace "Jun. 1996" with -- Jun. 1966 --.

Signed and Sealed this

Third Day of January, 2006

JON W. DUDAS
*Director of the United States Patent and Trademark Office*